Figure 1A:
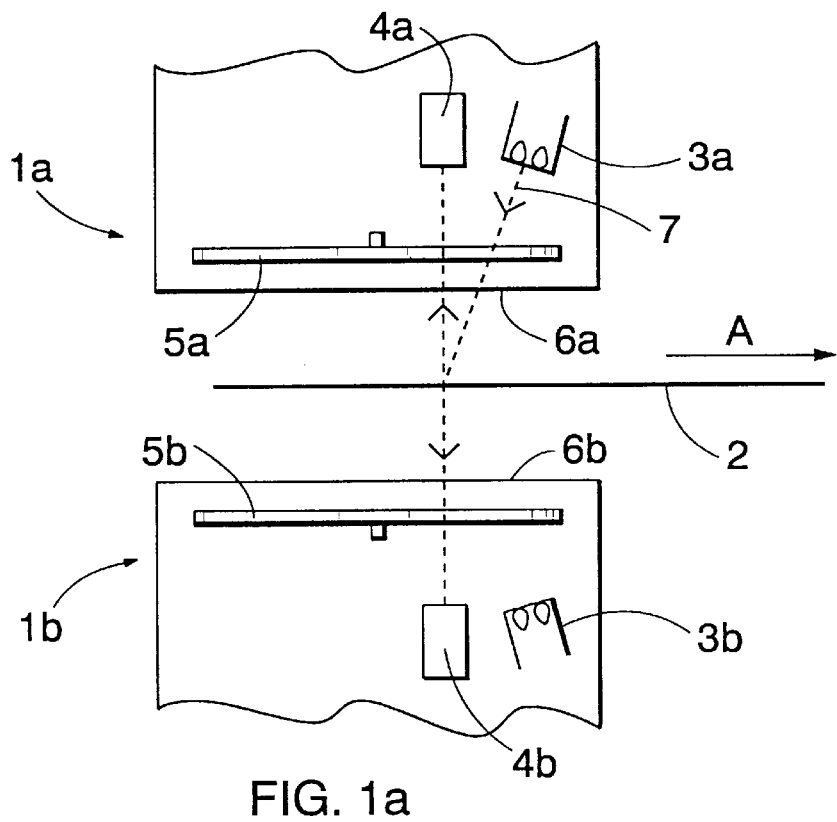

United States Patent [19]
Shakespeare et al.

[11] Patent Number: 5,991,046
[45] Date of Patent: Nov. 23, 1999

[54] METHOD AND APPARATUS FOR OPTICALLY MEASURING PROPERTIES OF A MOVING WEB

[75] Inventors: Tarja Shakespeare; John Shakespeare, both of Siuro, Finland

[73] Assignee: Valmet Automation Inc., Helsinki, Finland

[21] Appl. No.: 09/115,363

[22] Filed: Jul. 14, 1998

[51] Int. Cl.[6] .................................................. G01N 21/84
[52] U.S. Cl. .......................................... 356/429; 356/430
[58] Field of Search ..................................... 356/429, 430, 356/431, 237.1, 237.6, 238.1, 238.3, 239.1, 239.8

[56] References Cited

U.S. PATENT DOCUMENTS

| | | | |
|---|---|---|---|
| 4,389,575 | 6/1983 | Cole | 356/430 |
| 4,565,444 | 1/1986 | Mactaggart | 356/73 |
| 4,737,649 | 4/1988 | Naruse | 356/430 |
| 4,801,809 | 1/1989 | Burk et al. | 250/559 |
| 5,377,279 | 12/1994 | Hanafusa et al. | 356/430 |

Primary Examiner—Robert H. Kim
Assistant Examiner—Amanda Merlino
Attorney, Agent, or Firm—Ladas & Parry

[57] ABSTRACT

The invention relates to a method and apparatus for measuring and controlling optical properties of a moving web. Sensor heads are installed in the same location on the opposite sides of the web to be measured so that there is at least one means of illuminating the web and at least one means of detecting radiances on both sides of the web. At least one means of illuminating the web of at least one side is controlled so as to provide at least two different lighting states. Measuring the values in different lighting states with both means of detecting radiances simultaneously allows determination the optical properties of the web on its both sides.

16 Claims, 3 Drawing Sheets

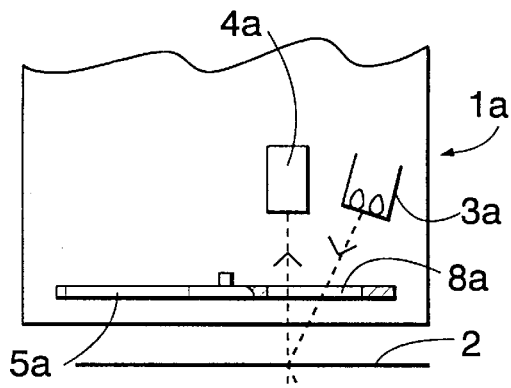
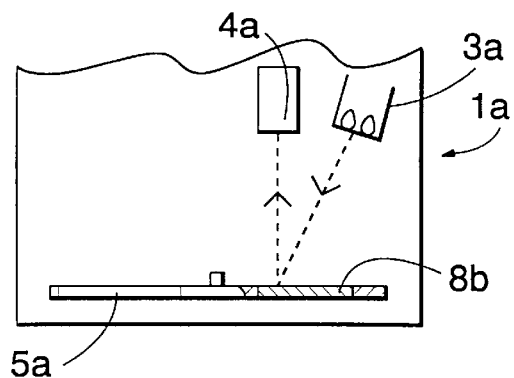
FIG. 3a                    FIG. 3b
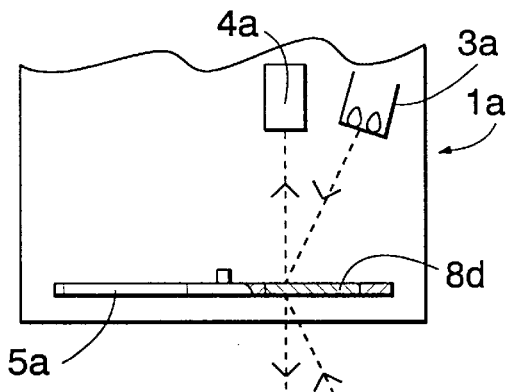
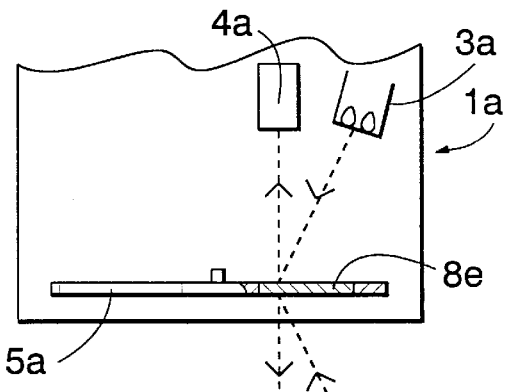
FIG. 3c                    FIG. 3d

METHOD AND APPARATUS FOR OPTICALLY MEASURING PROPERTIES OF A MOVING WEB

The invention relates to a method for optically measuring properties of a moving web.

The invention further relates to apparatus for optically measuring properties of a moving web, the apparatus comprising a first sensor head, which comprises a means of illuminating the web and a means of detecting radiances, a second sensor head, which comprises a means of illuminating the web and a means of detecting radiances.

Optical properties of paper, especially color, brightness and related quantities, are measured with a gauge from one surface of the paper by using reflection measurement, whereby the light source and detector of the gauge are on the same side of the web to be measured. Additional optical properties, such as opacity and related quantities, are often derived from differences in measurements of the above-mentioned optical properties with different backing conditions on the opposite side of the web. These methods are commonly known to those skilled in the art. Methods of approximately separating measured radiances into their reflective and fluorescent components are also well known. Properties of paper differ between the two sides of the sheet, and this difference can be large, especially on multi-layer sheets. To measure optical properties of the opposite surface, another gauge is needed. Such a solution is unwieldy and expensive, and subject to inaccuracies caused by imperfect correlation between the gauges. The properties of the web are also measured in two different locations in solutions based on scanning or fixed point measurement.

U.S. Pat. No. 4,565,444 discloses a first solution which avoids scanning by providing plural means of illumination and corresponding means of detecting light deployed at different positions across the web, and a second solution which employs light pipes to convey light from means of illumination to several locations on the web, and light pipes to convey the reflected and transmitted light from the same locations to a means of detecting light. In these solutions, measurements of reflected light at plural wavelength bands are used to measure the color, brightness, and other properties of the web, and measurements of transmitted light at plural wavelength bands are used to measure opacity and other properties of the web. U.S. Pat. No. 4,801,809 discloses a solution similar to the first solution of U.S. Pat. No. 4,565,444, wherein a strip across the web is illuminated, and measurements of transmitted and reflected light at several wavelength bands are made at plural locations across the web, and properties of the web are measured using said light measurements. To measure properties of the opposite side of the web and the opacity in the opposite direction, another gauge is needed, and thus the drawbacks of the solution disclosed in the publication are the same as those described above.

An object of the invention is to provide a method and apparatus which allow the above-mentioned drawbacks to be avoided, and which provides numerous other advantages compared to the trivial solution of using two independent one-sided measurement devices.

The method of the invention is characterized in that sensor heads are installed in the same location on both sides of the web to be measured so that there is at least one means of illuminating the web and at least one means of detecting radiances on both sides of the web, wherein at least one means of illuminating the web of at least one side is controlled so as to provide at least two different lighting states, and the means of detecting radiances on the different sides of the web simultaneously carry out measurements in at least two of the different lighting states, and thus the optical properties of the web can be determined on both sides of the web by measuring the values in different lighting situations.

The apparatus of the invention is characterized in that the first sensor head and the second sensor head are installed in the same location on the different sides of the web to be measured, so that both means of detecting radiances are arranged to measure radiances transmitted or reflected by the web from both means of illuminating the web.

The basic idea of the invention is that sensor heads are installed in the same location on the opposite sides of the web to be measured, whereby there is at least one means of illuminating the web and at least one means of detecting radiances on both sides of the web. At least one means of illuminating the web of at least one side is controlled so as to provide at least two different lighting situations. At least one means of detecting radiances on each side of the web carry out measurements simultaneously. Measuring the values in different lighting situations allows determination of optical properties of the web on each side. The idea of a preferred embodiment of the invention is that sensor heads installed on the different sides of the web are substantially identical in at least one means of illuminating the web and at least one means of detecting radiances. In another preferred embodiment, the sensor heads are substantially identical, and are interchangeable in whole or in their component parts.

An advantage of the invention is that correlation and calibration of the units on the opposite sides of the web can be implemented very accurately. Furthermore, the transmittance measurement of opacity can be easily carried out through the web in both directions, so that effects of differences in fluorescence and absorption between the two sides of the web can be more accurately determined. In addition, since the measuring units are identical, their manufacturing and maintenance costs can be minimized.

For the purpose of this specification and claims the term "optical properties" includes also optical properties which are not directly visible to humans but which are measured optically.

Figure 1B:
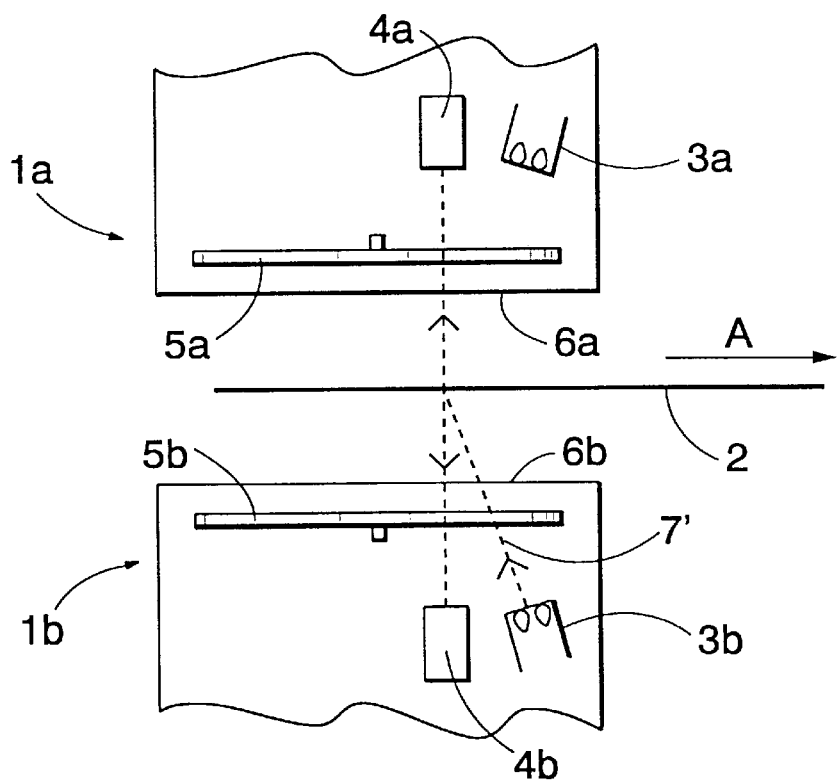
Figure 2:
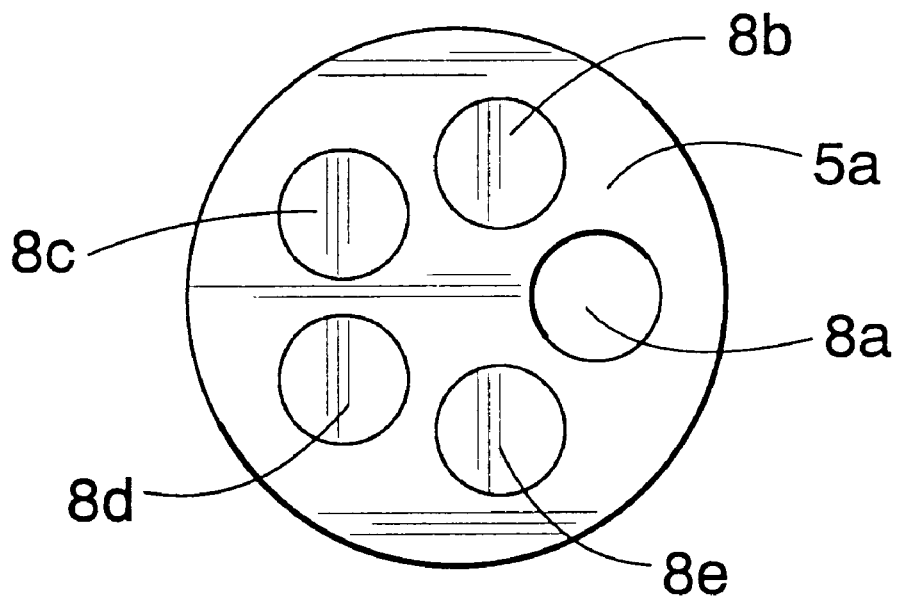
Figure 4:
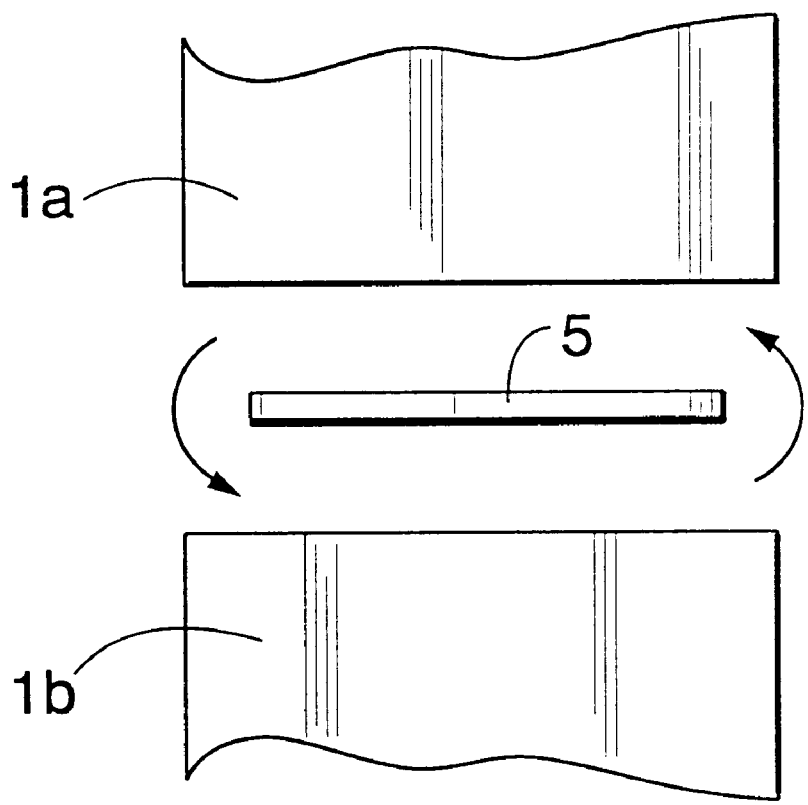

The invention will be described in greater detail in the accompanying drawings, in which FIGS. 1a and 1b are schematic side views of a solution of the invention, FIG. 2 is a top view of a calibration unit of the apparatus according to FIGS. 1a and 1b, FIGS. 3a to 3d are schematic side views of a solution of the invention and FIG. 4 is a schematic side view of another solution of the invention.

FIG. 1a illustrates an apparatus comprising a first sensor head 1a and a second sensor head 1b between which a paper web 2 is arranged. The web 2 moves in the machine direction according to arrow A. The first sensor head 1a and the second sensor head 1b are preferably arranged to a measuring frame, in which the sensor heads 1a and 1b move substantially continuously in a direction transverse to the machine direction. For the sake of clarity the measuring frame is not shown in the figures. The optical properties of the paper web 2 are measured substantially continuously as the paper web 2 moves forward. The web of paper, paperboard or tissue is one example of a moving sheet the optical properties of which are measured with the solution of the invention.

The first sensor head 1a comprises at least one means 3a of illuminating the web with radiance suitable for purposes of measurement. At least one means of detecting radiances 4a measures the amount of radiance incident on it. The sensor heads 1a and 1b may comprise plural means of illuminating the web, where not at all such means are identical in spectral distribution of radiant energy and geometry relative to the web. The sensor heads 1a and 1b may further comprise plural means of detecting radiances, where not all such means are identical in spectral sensitivity to radiant energy and geometry relative to the web. In one embodiment, a means of detecting radiances measures the radiance in each of several wavelength bands substantially spanning at least the visible range using for example, a monochromator and an array of responsive elements, or a filter wheel or moving variable filter with one responsive element. A means of detecting radiances may additionally or alternatively measure the radiance in each of at least one wavelength band in the infra-red or at longer wavelengths. A means of detecting radiances may additionally or alternatively measure tristimulus X, Y, Z or brightness or opacity or other optical property by means of specific light filters, each with a responsive element, or by means of interposable light filters sharing the same responsive element. The first sensor head 1a further comprises a calibration unit 5a. The beam 7 used in measuring goes through the sensor window 6a against the paper web 2. The second sensor head 1b, like the first sensor head 1a, comprises at least one means 3b of illuminating the web, at least one means 4b of detecting radiances, calibration unit 5b and sensor window 6b. The first sensor head 1a and the second sensor head 1b are preferably very similar in structure, such as by comprising substantially identical components interchangeable between the two sensor heads, where the arrangement of components within the two sensor heads are mirror or rotational images of each other. Most preferably, the two sensor heads 1a and 1b are substantially identical in structure and are interchangeable, comprising substantially identical components interchangeable between the two sensor heads, arranged substantially identically in both sensor heads.

The simplest way of measuring with the apparatus of the invention is to send a beam 7 from a means of illuminating the web 3a of the first sensor head 1a at the first stage, as is shown in FIG. 1a. In that case a means of detecting radiances 4a of the first sensor head 1a measures the beam reflected from the paper web 2. A means of detecting radiances 4b of the second sensor head 1b simultaneously measures the beam that has gone through the paper web 2. At the second stage illumination of the web by the means of illuminating the web 3a of the first sensor head 1a is interrupted, and a beam 7' is generated by a means of illuminating the web 3b of the second sensor head 1b according to the FIG. 1b. In that case a means of detecting radiances 4b of the second sensor head 1b measures the beam reflected from the paper web 2, and a means of detecting radiances 4a of the first sensor head 1a measures the beam that has gone through the paper web 2. Illumination of the web by the means 3a and 3b is most preferably intermittent in operation or interruptable, either by use of a flashing source of radiant energy or by means of interrupting the radiant flux from a continuous source of radiant energy, or blocking the optical path to the web, or diverting the radiance so that it does not illuminate the web. After the measurements have been carried out, various optical and related properties can be determined for the two sides of the web. For example, the optical properties which would be measured for either side of a stack, each layer of the stack having the same properties as the web and in the same orientation, can be determined by means of Kubelka-Munk or other models; printing opacity and infinite pad color can be estimated in this way. As another example, the optical properties of the web which would be measured if it had a backing of known optical properties, can be determined for either orientation of the web with respect to the backing; TAPPI opacity can be estimated in this way with a backing of uniform 89% reflectance in the visible range. Measurements made of optical reflectance and transmittance of infra-red and other wavelength bands can be used to determine various optical-related properties of the web, including differences in said properties between the two sides of the web.

FIG. 2 is a top view of the calibration unit 5a. The calibration unit 5a is of the carousel type, and it preferably comprises at least 5 different operating elements. One operating element 8a is a hole in the calibration unit 5a, and the beam 7 passes through the hole 8a in a normal measuring situation. A second operating element 8b is a non-glossy non-fluorescent reference of known high diffuse reflectivity for white level calibration. A third operating element 8c is a black reference such as a cavity or other light trap, or a non-glossy non-fluorescent black tile of known low diffuse reflectivity for black level calibration. A fourth operating element 8d is a non-glossy, non-fluorescent translucent reference of known diffuse transmittance for transmittance measurement and can also be used for assessment of and compensation for aging of optical components such as lamps. There may be plural references 8b and 8c for white and black level calibration of different wavelength bands, or for different means of illuminating the web or for different means of detecting radiances. Additional references may also be provided, depending on the types and relative geometries of means of illuminating the web and means of detecting radiances. For example, reference elements may include a non-scattering translucent reference of known directional transmittance, or a specular element of known specular reflectivity, or a glossy non-fluorescent reference of known gloss factors, or a non-glossy fluorescent reference of known fluorescence factors and known diffuse reflectance. In the illustrated embodiment, operating elements 8b and 8c are meant for calibration of a means of detecting radiances in the first sensor head, with respect to a means of illuminating the web in the same sensor head. Operating element 8d is meant for calibration of a means of detecting radiances in the first sensor head, with respect to a means of illuminating the web in the second sensor head. A fifth operating element 8e is another non-glossy non-fluorescent reference of known high diffuse reflectivity which is upside-down with respect to the reference 8b. Operating element 8e is used to measure the optical purity of the sensor windows 6a and 6b by illuminating it with a means of illumination 3b in the second sensor head and measuring the reflected radiances with a means of detecting light 4b in the second sensor head 1b. In that case there naturally is no paper web 2 between the measuring heads 1a and 1b. For the measurement to be accurate the reflectivity of the measuring windows 6a and 6b must be as low as possible or the reflectivity and transmissivity of the windows has to be known. The calibration unit 5b of the second sensor head 1b naturally corresponds to the calibration unit 5a with operating elements which are substantially the same as those of the calibration unit 5a.

In the case that calibration units such as 5a and 5b are within the sensor heads 1a and 1b, some components of each sensor head, such as means of illuminating the web 3a and 3b or means of detecting radiances 4a and 4b, may be movable perpendicularly to suitable set positions in relation to the plane of the web. By displacing relevant components in the first sensor head 1a further from the plane of the web during calibration, by an amount approximately equal to the distance from the plane of the web to the surface of the reference elements 8b and 8c in the first sensor head, the relative geometry of illumination and detection of radiances with respect to the reference elements 8b and 8c in the first sensor head during calibration can be made essentially the same as their relative geometry with respect to the web 2 during normal operation. Using, for example, the normal measuring geometry depicted in FIG. 3a, this calibration geometry is illustrated in FIG. 3b for simultaneous calibration using the elements 8b and 8b' in the first and second sensor heads respectively. Similarly, by suitably displacing relevant components in the second sensor head 1b closer to the plane of the web during calibration, by an amount approximately equal to the distance from the plane of the web to the surface of the reference element 8e in the first sensor head, the relative geometry of means of illuminating the web 3b and means of detecting radiances 4b in the second sensor head with respect to the reference element 8e in the first sensor head 1a can be kept the same as their relative geometry with respect to the web 2 during normal operation, as depicted in FIG. 3d. Note that FIG. 3d is drawn so that the reverse side of the reference 8e may contain another reference such as 8b, for use simultaneously in calibration by the means of illumination 3a and means of detecting radiances 4a in the first sensor head. Furthermore, by suitably displacing relevant components in the second sensor head 1b closer to the plane of the web, by an amount approximately equal to the distance from the plane of the web to the reference element 8d in the first sensor head, and displacing relevant components in the first sensor head 1a further from the plane of the web by an amount approximately equal to the distance from the plane of the web to the reference element 8d in the first sensor head, and relative geometry of means of illuminating the web 3a, 3b and means of detecting radiances 4a, 4b by both sensor heads with respect to the reference element 8d in the first sensor head 1a during calibration can be kept the same as their relative geometry with respect to the web 2 during normal operation, as depicted in FIG. 3c. Thus, the set positions for movement of components of the first sensor head should be the normal operating position, and displacements from that position corresponding approximately to the distances from the plane of the web to the reference element mentioned above. The relevant components in the second sensor head 1b can be movable in like fashion, and for like purposes. Note that the displacements need not be linear, and may occur in directions other than perpendicular to the plane of the web, and components other than the means of illumination and means of detecting radiances may be displaceable for calibration purposes. Note also, that for certain constructions of a sensor head, the means of illuminating the web and the means of detecting radiances may be positioned that by rotating them away from their normal alignment, it may be possible to present references in a relative geometry which is similar to their geometry relative to the web in normal operation. This is advantageous in that usually a means of rotation are mechanically more reliable and simpler to construct than a means of displacement. However, such an arrangement does not permit measurement of the optical properties of the sensor windows 6a and 6b, and so is less advantageous in terms of accuracy of calibration of the apparatus.

FIG. 4 is a side view of another solution of the invention. In the solution of FIG. 4 the calibration unit 5 is arranged at the same location as the paper web 2 would be between the sensor heads 1a and 1b, i.e. calibration is performed at the normal site of passage of the paper web. A calibration unit 5 may be deployed only when there is no web in the gap between sensor heads, but may be utilized by both sensor heads. When the calibration unit 5 is at the same location as the paper web 2 would be, its distance from the measuring heads 1a and 1b is optimal. Furthermore, the calibration unit 5 is arranged outside the measuring heads 1a and 1b, and thus it also takes into account dirt and scratching on the windows of the sensor heads as well as other impurities. The calibration unit 5 is preferably turnable according to the arrows in FIG. 4, so that it can be flipped upside down, whereby exactly similar calibration can be performed on both measuring heads 1a and 1b. In the case that the calibration unit 5 can be flipped, it needs at least three operating elements—a white reference such as 8b, a black reference such as 8c, and a translucent reference such as 8d. Alternatively, the individual elements of the calibration unit 5 can be flipped without the need to flip the entire unit, and allowing such flipping to occur in a smaller space. In the case that the individual elements of the calibration unit 5 can be flipped, it similarly needs at least three operating elements—a flippable white reference such as 8b, a flippable black reference such as 8c, and a translucent reference such as 8d which need not be flippable. In the case that neither the operating elements of the calibration unit 5, nor the unit itself can be flipped, it needs at least five operating elements—a black reference and a white reference, both oriented towards the first sensor head, another black reference and another white reference, both oriented towards the second sensor head, and a translucent reference. Black and white references, being opaque, can occupy the same position in the carousel for a reference oriented to the first sensor head and a reference oriented to the second sensor head, so that both sensor heads can be calibrated simultaneously for black and white references.

Since the calibration unit 5 must be retracted during measurement of the web, an operating element with a hole is not needed. Furthermore, since a calibration unit 5 can be shared between sensor heads, it is not necessary to equip both sensor heads with a calibration unit such as 5. Preferably, a shared calibration unit 5, which can be deployed in the location between the sensor heads which corresponds to the normal paper path is mounted externally to the sensor heads. For example in a scanning apparatus, it can be retracted into a housing in the end stanchion of the support beam for normal measuring operation, and deployed into the gap between the sensor heads when the traversing platform moves to a designated calibration position adjacent to the end stanchion.

By suitably illuminating the web on either side with radiances of suitably chosen characteristics, and measuring the amounts of radiances reflected and transmitted on both sides, a number of related properties can be deduced. For example, in a paper web comprising some recycled paper pulp, presence of residual ink can be determined from transmission and reflection of infra-red radiances of 950 nm wavelength; the difference in distribution of residual ink between the two sides can be determined from the measurements on both sides. Similarly, the presence of one or more substances as constituents of the web can be determined from the relative shapes of the reflectance and transmittance spectra at infra-red and longer wavelengths; the difference in distribution of said components between the two sides of the sheet can be determined from the measurements on both sides. The invention contemplates and encompasses measurement of optical properties on both sides of the web in wavelength bands outside the visible range, including ultraviolet and infra-red ranges, and estimation of diverse properties of the web which are related to said properties, especially differences in said estimated properties between the two sides of the web.

The drawings and the related description are only intended to illustrate the inventive idea. The details of the invention may vary within the scope of the claims. Thus there may be plural light sources on one or both sides of the web, and their power may be controlled so as to provide an appropriate intensity of illumination. An arrangement may also be provided for measuring the intensity of radiances produced by a means of illumination, including measurement of total radiant energy and of distribution of radiant energy among several wavelength bands. Said arrangement may be by provision of additional means of radiances detection with suitable beam splitting or beam diverting means, such as in a dual-beam spectrophotometer. Said arrangement may alternatively be by use of the existing means of detection of radiances with suitable beam diverting means to intermittently measure the radiances produced by a means of illumination instead of measuring the radiances incident during normal operation. Furthermore, to provide different lighting situations it is not necessary to extinguish the light source or light sources of the opposite side, but it is sufficient that at least one light source of at least one side is controlled so as to provide two different illumination situations. Radiances are measured at both sensor heads simultaneously under active illumination. A simple example of a pattern of illumination is that the web is illuminated by each sensor head alternately. An alternative example is that the web is illuminated from one sensor head in all states of illumination, while the illumination from the other sensor head is different in each of several states. Obviously, the illumination from both sensor heads may be different in each of the states of illumination.

Some example sequences of illumination conditions are for instance: (I) A, B, A, B, . . . , (II) A, A', B, A, A', B, . . . , (III) A, A+B, B, A, A+B, B, . . . (IV) A+B, A'+B, A'+B', A+B', A+B . . . , (V) A, B, A+B, A', B', A'+B', A", B", A"+B", A, B, . . . in which the individual illumination conditions are:

| | |
|---|---|
| A | sensor head 1 illuminating web with its state 1 |
| | sensor head 2 not illuminating web |
| A' | sensor head 1 illuminating web with its state 2 |
| | sensor head 2 not illuminating web |
| A" | sensor head 1 illuminating web with its state 3 |
| | sensor head 2 not illuminating web |
| B | sensor head 1 not illuminating web |
| | sensor head 2 illuminating web with its state 1 |
| B' | sensor head 1 not illuminating web |
| | sensor head 2 illuminating web with its state 2 |
| B" | sensor head 1 not illuminating web |
| | sensor head 2 illuminating web with its state 3 |
| A + B | sensor head 1 illuminating web with its state 1 |
| | sensor head 2 illuminating web with its state 1 |
| A' + B | sensor head 1 illuminating web with its state 2 |
| | sensor head 2 illuminating web with its state 1 |
| A + B' | sensor head 1 illuminating web with its state 1 |
| | sensor head 2 illuminating web with its state 2 |
| A' + B' | sensor head 1 illuminating web with its state 2 |
| | sensor head 2 illuminating web with its state 2 |
| etc. | |

The examples above are all simple periodic patterns of illumination conditions, but the invention also encompasses random, pseudo-random, quasi-periodic, and other aperiodic sequences, including illumination patterns in which the conditions of illumination in a state depend on measurements made in previous states as well as on the conditions of illumination in those states. Moreover, whether the pattern of illumination is deterministic, periodic, or random, the various conditions of web illumination need not all occur with equal frequency.

In addition, the location of the light source or the measuring head can be changed with respect to the web thereby changing the direction of incidence of the light in the machine direction or in the cross direction. Furthermore, the measuring geometry of the apparatus is not bound to any particular value, but the measuring geometry of the apparatus of the invention may vary in a manner known per se. The invention applies especially to instrument geometries which have been recommended in standards issued by authorities such as CIE for measurement of color, including 0/45, 45/0, 8/$d$, $d$/18, 0/$d$ and $d$/0 configurations. The directional component of the geometry may be at a single direction at the specified angle to the normal, at several such discrete directions sequentially or simultaneously, or at an arc or annulus subtending the specified angle to the normal. The diffuse component of the geometry, if any, may optionally employ a gloss trap for exclusion of the specular component of reflection or the direct component of transmission.

The invention contemplates and encompasses apparatus capable of plural instrument geometries, sequentially or simultaneously. For example, in one embodiment, transmitted radiances are measured using at least two means of detecting radiances in the first sensor head, each measuring directional radiances at a different angle to the path of incidence onto the web of directional radiances from a means of directionally illuminating the web in the second sensor head. Thus, the scattering and absorptive effects of the web can be independently measured. In another embodiment, remitted radiances are measured using at least two means of detecting radiances in the first sensor head, each measuring directional radiances at a different angle to the path of incidence onto the web of directional radiances from a means of directionally illuminating the web in the first sensor head. Thus the effects of specular reflection and diffuse reflection can be independently measured. The Lambertian nature of reflection and transmission results in a commutativity between detector and source geometries. Thus, measurement with a single detector and multiple source geometries is equivalent to measuring with multiple sources and a single detector, in the same relative geometrical arrangement.

The calibration unit may also be of the shape of a cut ring, whereby the calibration elements can be placed in the location of the paper web between the measuring heads at the moment of calibration. The calibration elements may be two-sided, in which case only one calibration ring is needed. Furthermore, the calibration element can be arranged vertically, and the beams can be directed against the surface of the tile by means of two different prisms, and thus the beam of both the measuring heads focuses on the same surface in the calibration, which yields a very good accuracy of calibration.

If desired, an appropriate filter can be installed in front of the light source, detector or both of them. There may also be several filters, if necessary. Plural filters may be used singly, sequentially, or in combination to control the character of the radiances illuminating the web, or the character of the radiances incident on a means of detecting radiances.

The properties to be measured with the present invention include not only color but also spectral radiance factors for transmittance and reflectance on both sides of the moving web, including separate determination of their fluorescence components, and including parametrization of said properties as reflectance, transmittance, and fluorescence factors. Said properties are measured in at least one range of visible, ultra-violet, or infra-red wavelengths, where plural such ranges need not be non-overlapping in wavelengths and need not be contiguous. At least one value is measured for at least one of said properties in at least one of said measurement ranges for both sides of the web, and said value may represent a weighted or unweighted average of radiances in said range. Said measurement ranges may be further subdivided into substantially contiguous wavelength bands which need not be equal, and in each of which a value is measured for at least one of said properties, for both sides of the sheet Although the methods, apparatus, details, and embodiments of the present invention have been described for application to a moving web, it should be understood that it has similar applicability for certain other processes, and especially for a stationary web, or for a moving or stationary sheet, or for a moving or stationary film. Application of the disclosed methods and apparatus to measurement of optical and related properties, characterization of the effects of process modulation on said properties, or control of optical or related properties in these and other similar processes is contemplated by, and within the scope of the invention.

We claim:

1. A method for optically measuring properties of a moving web, in which method sensor heads are installed in the same location on both sides of the web to be measured so that there is at least one means of illuminating the web and at least one means of detecting radiances on both sides of the web, wherein at least one means of illuminating the web of at least one side is controlled so as to provide at least two different lighting states, and the means of detecting radiances on the different sides of the web simultaneously carry out measurements in at least two of the different lighting states, and thus the optical properties of the web can be determined on both sides of the web by measuring the values in different lighting situations.

2. A method as claimed in claim 1, wherein the measuring is performed at two stages in such a manner that at the first stage only the first means of illuminating the web illuminates the web with radiance and the means of detecting radiances on both sides of the web carry out measurements, and at the second stage only the second means of illuminating the web illuminates the web with radiance and the means of detecting radiances on both sides of the web carry out measurements.

3. A method as claimed in claim 1, wherein the sensor heads on the different sides of the web have a substantially identical structure.

4. A method as claimed in claim 1, wherein the measured properties for the two sides of the web are used to estimate the properties of one or both side of a stack whose layers each have properties identical to the web properties and where each layer has a known orientation.

5. A method as claimed in claim 1, wherein the measured properties for the two sides of the web, together with known properties of a material to be used as a backing, are used to estimate the properties of either side of the combination of the web in either orientation with respect to the backing material.

6. A method as claimed in claim 1, wherein the measured properties for the two sides of the web are measured at each of plural wavelength bands in the visible range.

7. A method as claimed in claim 1, wherein the measured properties for the two sides of the web are measured at each of plural wavelength bands in the ultra-violet range.

8. A method as claimed in claim 1, wherein the measured properties for the two sides of the web are measured at each of plural wavelength bands in the infra-red range.

9. A method as claimed in claim 1, wherein the moving web is a moving web of paper, paperboard, or tissue.

10. An apparatus for optically measuring properties of a moving web, the apparatus comprising:

a first sensor head for illuminating the web and detecting radiances therefrom; and a second sensor head for illuminating the web and detecting radiances therefrom, wherein the first sensor head and the second sensor head are in corresponding locations on opposite sides of the web so that the detecting of radiances of both measure radiances transmitted and reflected from the web.

11. An apparatus as claimed in claim 10, wherein the first sensor head and the second sensor head have a substantially identical structure.

12. An apparatus as claimed in claim 10, the apparatus comprising at least one calibration unit, which comprises at least one calibration reference which is upside-down with respect to other calibration references.

13. An apparatus as claimed in claim 10, the apparatus comprising at least one calibration unit which is installed during the calibration substantially in the position between the sensor heads in which the web normally passes in measurement operation.

14. An apparatus as claimed in claim 13, wherein the calibration unit or some of the calibration references therein can be turned upside-down.

15. An apparatus as claimed in claim 12, wherein the illuminating of the web and the detecting of radiances from the web of both of the sensor heads have substantially the same geometrical relation to the calibration references during the calibration as they have to the web during the illuminating and detecting.

16. A method for detecting for optically measuring properties of a moving web, the method comprising:

locating sensor heads at corresponding locations on opposite sides of a moving web; and illuminating the web and detecting transmitted and reflected radiances from the web in the sensor heads for optically measuring properties of the web, wherein the illuminating of the web of at least one of the sensor heads is at least at two different lighting states, and the detecting of the radiances by the sensor heads is simultaneous and at the at least two different lighting states.

* * * * *